(12) United States Patent
Lee et al.

(10) Patent No.: US 12,728,203 B2
(45) Date of Patent: Sep. 8, 2026

(54) TECHNIQUES FOR RECOMMENDING RESCUE CARBOHYDRATE INGESTION IN AUTOMATIC MEDICATION DELIVERY SYSTEMS

(71) Applicant: INSULET CORPORATION, Acton, MA (US)

(72) Inventors: Joon Bok Lee, Acton, MA (US); Matthew Alles, Winchester, MA (US); Yibin Zheng, Hartland, WI (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 1097 days.

(21) Appl. No.: 17/860,609

(22) Filed: Jul. 8, 2022

(65) Prior Publication Data

US 2023/0011699 A1 Jan. 12, 2023

Related U.S. Application Data

(60) Provisional application No. 63/220,824, filed on Jul. 12, 2021.

(51) Int. Cl.
*A61M 5/172* (2006.01)

(52) U.S. Cl.
CPC ....... *A61M 5/1723* (2013.01); *A61M 2205/18* (2013.01); *A61M 2205/502* (2013.01); *A61M 2205/52* (2013.01); *A61M 2230/201* (2013.01)

(58) Field of Classification Search
None
See application file for complete search history.

(56) References Cited

U.S. PATENT DOCUMENTS

| | | | |
|---|---|---|---|
| 303,013 | A | 8/1884 | Horton |
| 2,797,149 | A | 6/1957 | Skeggs |

(Continued)

FOREIGN PATENT DOCUMENTS

| | | | |
|---|---|---|---|
| AU | 2015200834 | A1 | 3/2015 |
| AU | 2015301146 | A1 | 3/2017 |

(Continued)

OTHER PUBLICATIONS

US 5,954,699 A, 09/1999, Jost et al. (withdrawn)

(Continued)

*Primary Examiner* — Manuel A Mendez
(74) *Attorney, Agent, or Firm* — Goodwin Procter LLP

(57) ABSTRACT

Provided are techniques, devices and systems that include monitoring a trend of blood glucose measurement values over a series of measurement cycles. A processor may identify a potential excursion outside a range of a target blood glucose measurement value setting of a user based on the monitored trend. In response to the identified potential excursion, an alert may be generated to the user to consume rescue carbohydrates. In addition, the disclosed techniques may include a processor that assesses the factors related to a potential impending hypoglycemic event for a user. Based on a result of the assessment of the factors, the processor may determine whether the user is approaching the potential impending hypoglycemic event for the user. In response to a determination that the user is approaching the potential impending hypoglycemic event for the user, a number of rescue carbohydrates to suggest for consumption by the user may be determined.

4 Claims, 7 Drawing Sheets

(56) References Cited

U.S. PATENT DOCUMENTS 3,631,847 A 1/1972 Hobbs
3,634,039 A 1/1972 Brondy
3,812,843 A 5/1974 Wootten et al.
3,841,328 A 10/1974 Jensen
3,963,380 A 6/1976 Thomas, Jr. et al.
4,055,175 A 10/1977 Clemens et al.
4,146,029 A 3/1979 Ellinwood, Jr.
4,151,845 A 5/1979 Clemens
4,245,634 A 1/1981 Albisser et al.
4,368,980 A 1/1983 Aldred et al.
4,373,527 A 2/1983 Fischell
4,403,984 A 9/1983 Ash et al.
4,464,170 A 8/1984 Clemens et al.
4,469,481 A 9/1984 Kobayashi
4,475,901 A 10/1984 Kraegen et al.
4,526,568 A 7/1985 Clemens et al.
4,526,569 A 7/1985 Bernardi
4,529,401 A 7/1985 Leslie et al.
4,559,033 A 12/1985 Stephen et al.
4,559,037 A 12/1985 Franetzki et al.
4,573,968 A 3/1986 Parker
4,624,661 A 11/1986 Arimond
4,633,878 A 1/1987 Bombardieri
4,657,529 A 4/1987 Prince et al.
4,685,903 A 8/1987 Cable et al.
4,731,726 A 3/1988 Allen, III
4,743,243 A 5/1988 Vaillancourt
4,755,173 A 7/1988 Konopka et al.
4,781,688 A 11/1988 Thoma et al.
4,781,693 A 11/1988 Martinez et al.
4,808,161 A 2/1989 Kamen
4,854,170 A 8/1989 Brimhall et al.
4,886,499 A 12/1989 Cirelli et al.
4,900,292 A 2/1990 Berry et al.
4,919,596 A 4/1990 Slate et al.
4,925,444 A 5/1990 Orkin et al.
4,940,527 A 7/1990 Kazlauskas et al.
4,975,581 A 12/1990 Robinson et al.
4,976,720 A 12/1990 Machold et al.
4,981,140 A 1/1991 Wyatt
4,994,047 A 2/1991 Walker et al.
5,007,286 A 4/1991 Malcolm et al.
5,097,834 A 3/1992 Skrabal
5,102,406 A 4/1992 Arnold
5,109,850 A 5/1992 Blanco et al.
5,125,415 A 6/1992 Bell
5,134,079 A 7/1992 Cusack et al.
5,153,827 A 10/1992 Coutre et al.
5,165,406 A 11/1992 Wong
5,176,662 A 1/1993 Bartholomew et al.
5,178,609 A 1/1993 Ishikawa
5,207,642 A 5/1993 Orkin et al.
5,232,439 A 8/1993 Campbell et al.
5,237,993 A 8/1993 Skrabal
5,244,463 A 9/1993 Cordner, Jr. et al.
5,257,980 A 11/1993 Van Antwerp et al.
5,273,517 A 12/1993 Barone et al.
5,281,808 A 1/1994 Kunkel
5,299,571 A 4/1994 Mastrototaro
5,308,982 A 5/1994 Ivaldi et al.
5,342,298 A 8/1994 Michaels et al.
5,377,674 A 1/1995 Kuestner
5,380,665 A 1/1995 Cusack et al.
5,385,539 A 1/1995 Maynard
5,389,078 A 2/1995 Zalesky
5,411,889 A 5/1995 Hoots et al.
5,421,812 A 6/1995 Langley et al.
5,468,727 A 11/1995 Phillips et al.
5,505,709 A 4/1996 Funderburk et al.
5,505,828 A 4/1996 Wong et al.
5,507,288 A 4/1996 Bocker et al.
5,533,389 A 7/1996 Kamen et al.
5,558,640 A 9/1996 Pfeiler et al.
5,569,186 A 10/1996 Lord et al.
5,584,813 A 12/1996 Livingston et al.
5,609,572 A 3/1997 Lang
5,665,065 A 9/1997 Colman et al.
5,678,539 A 10/1997 Schubert et al.
5,685,844 A 11/1997 Marttila
5,685,859 A 11/1997 Kommerup
5,693,018 A 12/1997 Kriesel et al.
5,697,899 A 12/1997 Hillman et al.
5,700,695 A 12/1997 Yassinzadeh et al.
5,703,364 A 12/1997 Rosenthal
5,714,123 A 2/1998 Sohrab
5,716,343 A 2/1998 Kriesel et al.
5,722,397 A 3/1998 Eppstein
5,741,228 A 4/1998 Lambrecht et al.
5,746,217 A 5/1998 Erickson et al.
5,755,682 A 5/1998 Knudson et al.
5,758,643 A 6/1998 Wong et al.
5,800,405 A 9/1998 McPhee
5,800,420 A 9/1998 Gross et al.
5,801,057 A 9/1998 Smart et al.
5,804,048 A 9/1998 Wong et al.
5,817,007 A 10/1998 Fodgaard et al.
5,820,622 A 10/1998 Gross et al.
5,823,951 A 10/1998 Messerschmidt
5,840,020 A 11/1998 Heinonen et al.
5,848,991 A 12/1998 Gross et al.
5,851,197 A 12/1998 Marano et al.
5,858,005 A 1/1999 Kriesel
5,865,806 A 2/1999 Howell
5,871,470 A 2/1999 McWha
5,879,310 A 3/1999 Sopp et al.
5,902,253 A 5/1999 Pfeiffer et al.
5,931,814 A 8/1999 Alex et al.
5,932,175 A 8/1999 Knute et al.
5,935,099 A 8/1999 Peterson et al.
5,947,911 A 9/1999 Wong et al.
5,971,941 A 10/1999 Simons et al.
5,993,423 A 11/1999 Choi
5,997,501 A 12/1999 Gross et al.
6,017,318 A 1/2000 Gauthier et al.
6,024,539 A 2/2000 Blomquist
6,032,059 A 2/2000 Henning et al.
6,036,924 A 3/2000 Simons et al.
6,040,578 A 3/2000 Malin et al.
6,049,727 A 4/2000 Crothall
6,050,978 A 4/2000 Orr et al.
6,058,934 A 5/2000 Sullivan
6,066,103 A 5/2000 Duchon et al.
6,071,292 A 6/2000 Makower et al.
6,072,180 A 6/2000 Kramer et al.
6,077,055 A 6/2000 Vilks
6,090,092 A 7/2000 Fowles et al.
6,101,406 A 8/2000 Hacker et al.
6,102,872 A 8/2000 Doneen et al.
6,115,673 A 9/2000 Malin et al.
6,123,827 A 9/2000 Wong et al.
6,124,134 A 9/2000 Stark
6,126,637 A 10/2000 Kriesel et al.
6,128,519 A 10/2000 Say
6,142,939 A 11/2000 Eppstein et al.
6,143,164 A 11/2000 Heller et al.
6,157,041 A 12/2000 Thomas et al.
6,161,028 A 12/2000 Braig et al.
6,162,639 A 12/2000 Douglas
6,196,046 B1 3/2001 Braig et al.
6,200,287 B1 3/2001 Keller et al.
6,200,338 B1 3/2001 Solomon et al.
6,214,629 B1 4/2001 Freitag et al.
6,226,082 B1 5/2001 Roe
6,244,776 B1 6/2001 Wiley
6,261,065 B1 7/2001 Nayak et al.
6,262,798 B1 7/2001 Shepherd et al.
6,270,455 B1 8/2001 Brown
6,271,045 B1 8/2001 Douglas et al.
6,280,381 B1 8/2001 Malin et al.
6,285,448 B1 9/2001 Kuenstner
6,309,370 B1 10/2001 Haim et al.
6,312,888 B1 11/2001 Wong et al.
6,334,851 B1 1/2002 Hayes et al.
6,375,627 B1 4/2002 Mauze et al.

(56) References Cited

U.S. PATENT DOCUMENTS 6,379,301 B1 4/2002 Worthington et al.
6,402,689 B1 6/2002 Scarantino et al.
6,470,279 B1 10/2002 Samsoondar
6,475,196 B1 11/2002 Vachon
6,477,901 B1 11/2002 Tadigadapa et al.
6,484,044 B1 11/2002 Lilienfeld-Toal
6,491,656 B1 12/2002 Morris
6,512,937 B2 1/2003 Blank et al.
6,525,509 B1 2/2003 Petersson et al.
6,528,809 B1 3/2003 Thomas et al.
6,540,672 B1 4/2003 Simonsen et al.
6,544,212 B2 4/2003 Galley et al.
6,546,268 B1 4/2003 Ishikawa et al.
6,546,269 B1 4/2003 Kurnik
6,553,841 B1 4/2003 Blouch
6,554,798 B1 4/2003 Mann et al.
6,556,850 B1 4/2003 Braig et al.
6,558,351 B1 5/2003 Steil et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,125 B2 5/2003 Jepson et al.
6,572,542 B1 6/2003 Houben et al.
6,572,545 B2 6/2003 Knobbe et al.
6,574,490 B2 6/2003 Abbink et al.
6,575,905 B2 6/2003 Knobbe et al.
6,580,934 B1 6/2003 Braig et al.
6,618,603 B2 9/2003 Varalli et al.
6,633,772 B2 10/2003 Ford et al.
6,645,142 B2 11/2003 Braig et al.
6,653,091 B1 11/2003 Dunn et al.
6,662,030 B2 12/2003 Khalil et al.
6,669,663 B1 12/2003 Thompson
6,678,542 B2 1/2004 Braig et al.
6,699,221 B2 3/2004 Vaillancourt
6,718,189 B2 4/2004 Rohrscheib et al.
6,721,582 B2 4/2004 Trepagnier et al.
6,728,560 B2 4/2004 Kollias et al.
6,740,059 B2 5/2004 Flaherty
6,740,072 B2 5/2004 Starkweather et al.
6,751,490 B2 6/2004 Esenaliev et al.
6,758,835 B2 7/2004 Close et al.
6,780,156 B2 8/2004 Haueter et al.
6,810,290 B2 10/2004 Lebel et al.
6,837,858 B2 1/2005 Cunningham et al.
6,837,988 B2 1/2005 Leong et al.
6,846,288 B2 1/2005 Nagar et al.
6,862,534 B2 3/2005 Sterling et al.
6,865,408 B1 3/2005 Abbink et al.
6,890,291 B2 5/2005 Robinson et al.
6,936,029 B2 8/2005 Mann et al.
6,949,081 B1 9/2005 Chance
6,958,809 B2 10/2005 Sterling et al.
6,989,891 B2 1/2006 Braig et al.
6,990,366 B2 1/2006 Say et al.
7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis, III et al.
7,060,059 B2 6/2006 Keith et al.
7,061,593 B2 6/2006 Braig et al.
7,096,124 B2 8/2006 Sterling et al.
7,115,205 B2 10/2006 Robinson et al.
7,128,727 B2 10/2006 Flaherty et al.
7,139,593 B2 11/2006 Kavak et al.
7,139,598 B2 11/2006 Hull et al.
7,144,384 B2 12/2006 Gorman et al.
7,171,252 B1 1/2007 Scarantino et al.
7,190,988 B2 3/2007 Say et al.
7,204,823 B2 4/2007 Estes et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,497 B2 11/2007 Holmes et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,429,255 B2 9/2008 Thompson
7,460,130 B2 12/2008 Salganicoff
7,481,787 B2 1/2009 Gable et al.
7,491,187 B2 2/2009 Van Den Berghe et al.
7,500,949 B2 3/2009 Gottlieb et al.
7,509,156 B2 3/2009 Flanders
7,547,281 B2 6/2009 Hayes et al.
7,569,030 B2 8/2009 Lebel et al.
7,608,042 B2 10/2009 Goldberger et al.
7,651,845 B2 1/2010 Doyle, III et al.
7,680,529 B2 3/2010 Kroll
7,734,323 B2 6/2010 Blomquist et al.
7,766,829 B2 8/2010 Sloan et al.
7,785,258 B2 8/2010 Braig et al.
7,806,854 B2 10/2010 Damiano et al.
7,806,886 B2 10/2010 Kanderian, Jr. et al.
7,918,825 B2 4/2011 OConnor et al.
7,946,985 B2 5/2011 Mastrototaro et al.
7,972,296 B2 7/2011 Braig et al.
8,221,345 B2 7/2012 Blomquist
8,251,907 B2 8/2012 Sterling et al.
8,449,524 B2 5/2013 Braig et al.
8,452,359 B2 5/2013 Rebec et al.
8,454,576 B2 6/2013 Mastrototaro et al.
8,467,980 B2 6/2013 Campbell et al.
8,478,557 B2 7/2013 Hayter et al.
8,547,239 B2 10/2013 Peatfield et al.
8,597,274 B2 12/2013 Sloan et al.
8,622,988 B2 1/2014 Hayter
8,810,394 B2 8/2014 Kalpin
9,061,097 B2 6/2015 Holt et al.
9,171,343 B1 10/2015 Fischell et al.
9,233,204 B2 1/2016 Booth et al.
9,486,571 B2 11/2016 Rosinko
9,579,456 B2 2/2017 Budiman et al.
9,743,224 B2 8/2017 San Vicente et al.
9,907,515 B2 3/2018 Doyle, III et al.
9,980,140 B1 5/2018 Spencer et al.
9,984,773 B2 5/2018 Gondhalekar et al.
10,248,839 B2 4/2019 Levy et al.
10,335,464 B1 7/2019 Michelich et al.
10,583,250 B2 3/2020 Mazlish et al.
10,737,024 B2 8/2020 Schmid
10,987,468 B2 4/2021 Mazlish et al.
11,197,964 B2 12/2021 Sjolund et al.
11,260,169 B2 3/2022 Estes
2001/0021803 A1 9/2001 Blank et al.
2001/0034023 A1 10/2001 Stanton, Jr. et al.
2001/0034502 A1 10/2001 Moberg et al.
2001/0051377 A1 12/2001 Hammer et al.
2001/0053895 A1 12/2001 Vaillancourt
2002/0010401 A1 1/2002 Bushmakin et al.
2002/0010423 A1 1/2002 Gross et al.
2002/0016568 A1 2/2002 Lebel et al.
2002/0040208 A1 4/2002 Flaherty et al.
2002/0123740 A1 9/2002 Flaherty et al.
2002/0128543 A1 9/2002 Leonhardt
2002/0147423 A1 10/2002 Burbank et al.
2002/0155425 A1 10/2002 Han et al.
2002/0161288 A1 10/2002 Shin et al.
2003/0023148 A1 1/2003 Lorenz et al.
2003/0050621 A1 3/2003 Lebel et al.
2003/0060692 A1 3/2003 Ruchti et al.
2003/0086074 A1 5/2003 Braig et al.
2003/0086075 A1 5/2003 Braig et al.
2003/0090649 A1 5/2003 Sterling et al.

(56) References Cited

U.S. PATENT DOCUMENTS

2003/0100040 A1 5/2003 Bonnecaze et al.
2003/0130616 A1 7/2003 Steil et al.
2003/0135388 A1 7/2003 Martucci et al.
2003/0144582 A1 7/2003 Cohen et al.
2003/0163097 A1 8/2003 Fleury et al.
2003/0195404 A1 10/2003 Knobbe et al.
2003/0208113 A1 11/2003 Mault et al.
2003/0208154 A1 11/2003 Close et al.
2003/0212379 A1 11/2003 Bylund et al.
2003/0216627 A1 11/2003 Lorenz et al.
2003/0220605 A1 11/2003 Bowman, Jr. et al.
2004/0010207 A1 1/2004 Flaherty et al.
2004/0034295 A1 2/2004 Salganicoff
2004/0045879 A1 3/2004 Shults et al.
2004/0051368 A1 3/2004 Caputo et al.
2004/0064259 A1 4/2004 Haaland et al.
2004/0097796 A1 5/2004 Berman et al.
2004/0116847 A1 6/2004 Wall
2004/0122353 A1 6/2004 Shahmirian et al.
2004/0133166 A1 7/2004 Moberg et al.
2004/0147034 A1 7/2004 Gore et al.
2004/0171983 A1 9/2004 Sparks et al.
2004/0203357 A1 10/2004 Nassimi
2004/0204868 A1 10/2004 Maynard et al.
2004/0215492 A1 10/2004 Choi
2004/0220517 A1 11/2004 Starkweather et al.
2004/0241736 A1 12/2004 Hendee et al.
2004/0249308 A1 12/2004 Forssell
2005/0003470 A1 1/2005 Nelson et al.
2005/0020980 A1 1/2005 Inoue et al.
2005/0022274 A1 1/2005 Campbell et al.
2005/0033148 A1 2/2005 Haueter et al.
2005/0049179 A1 3/2005 Davidson et al.
2005/0065464 A1 3/2005 Talbot et al.
2005/0065465 A1 3/2005 Lebel et al.
2005/0075624 A1 4/2005 Miesel
2005/0105095 A1 5/2005 Pesach et al.
2005/0137573 A1 6/2005 McLaughlin
2005/0171503 A1 8/2005 Van Den Berghe et al.
2005/0182306 A1 8/2005 Sloan
2005/0192494 A1 9/2005 Ginsberg
2005/0192557 A1 9/2005 Brauker et al.
2005/0197621 A1 9/2005 Poulsen et al.
2005/0203360 A1 9/2005 Brauker et al.
2005/0203461 A1 9/2005 Flaherty et al.
2005/0238507 A1 10/2005 Dilanni et al.
2005/0261660 A1 11/2005 Choi
2005/0272640 A1 12/2005 Doyle, III et al.
2005/0277912 A1 12/2005 John
2006/0009727 A1 1/2006 OMahony et al.
2006/0079809 A1 4/2006 Goldberger et al.
2006/0100494 A1 5/2006 Kroll
2006/0134323 A1 6/2006 OBrien
2006/0167350 A1 7/2006 Monfre et al.
2006/0173406 A1 8/2006 Hayes et al.
2006/0189925 A1 8/2006 Gable et al.
2006/0189926 A1 8/2006 Hall et al.
2006/0197015 A1 9/2006 Sterling et al.
2006/0200070 A1 9/2006 Callicoat et al.
2006/0204535 A1 9/2006 Johnson
2006/0229531 A1 10/2006 Goldberger et al.
2006/0253085 A1 11/2006 Geismar et al.
2006/0264895 A1 11/2006 Flanders
2006/0270983 A1 11/2006 Lord et al.
2006/0276771 A1 12/2006 Galley et al.
2006/0282290 A1 12/2006 Flaherty et al.
2007/0016127 A1 1/2007 Staib et al.
2007/0060796 A1 3/2007 Kim
2007/0060869 A1 3/2007 Tolle et al.
2007/0060872 A1 3/2007 Hall et al.
2007/0083160 A1 4/2007 Hall et al.
2007/0106135 A1 5/2007 Sloan et al.
2007/0116601 A1 5/2007 Patton
2007/0118405 A1 5/2007 Campbell et al.
2007/0129690 A1 6/2007 Rosenblatt et al.
2007/0142720 A1 6/2007 Ridder et al.
2007/0173761 A1 7/2007 Kanderian et al.
2007/0173974 A1 7/2007 Lin et al.
2007/0179352 A1 8/2007 Randlov et al.
2007/0191716 A1 8/2007 Goldberger et al.
2007/0197163 A1 8/2007 Robertson
2007/0225675 A1 9/2007 Robinson et al.
2007/0244381 A1 10/2007 Robinson et al.
2007/0249007 A1 10/2007 Rosero
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0033272 A1 2/2008 Gough et al.
2008/0051764 A1 2/2008 Dent et al.
2008/0058625 A1 3/2008 McGarraugh et al.
2008/0065050 A1 3/2008 Sparks et al.
2008/0071157 A1 3/2008 McGarraugh et al.
2008/0071158 A1 3/2008 McGarraugh et al.
2008/0078400 A1 4/2008 Martens et al.
2008/0097289 A1 4/2008 Steil et al.
2008/0132880 A1 6/2008 Buchman
2008/0161664 A1 7/2008 Mastrototaro et al.
2008/0172026 A1 7/2008 Blomquist
2008/0177165 A1 7/2008 Blomquist et al.
2008/0188796 A1 8/2008 Steil et al.
2008/0200838 A1 8/2008 Goldberger et al.
2008/0206067 A1 8/2008 De Corral et al.
2008/0208113 A1 8/2008 Damiano et al.
2008/0214919 A1 9/2008 Harmon et al.
2008/0228056 A1 9/2008 Blomquist et al.
2008/0249386 A1 10/2008 Besterman et al.
2008/0269585 A1 10/2008 Ginsberg
2008/0269714 A1 10/2008 Mastrototaro et al.
2008/0269723 A1 10/2008 Mastrototaro et al.
2008/0287906 A1 11/2008 Burkholz et al.
2009/0006061 A1 1/2009 Thukral et al.
2009/0018406 A1 1/2009 Yodfat et al.
2009/0030398 A1 1/2009 Yodfat et al.
2009/0036753 A1 2/2009 King
2009/0043240 A1 2/2009 Robinson et al.
2009/0054753 A1 2/2009 Robinson et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0131861 A1 5/2009 Braig et al.
2009/0156922 A1 6/2009 Goldberger et al.
2009/0156924 A1 6/2009 Shariati et al.
2009/0163781 A1 6/2009 Say et al.
2009/0198350 A1 8/2009 Thiele
2009/0221890 A1 9/2009 Saffer et al.
2009/0228214 A1 9/2009 Say et al.
2009/0318791 A1 12/2009 Kaastrup
2009/0326343 A1 12/2009 Gable et al.
2010/0057042 A1 3/2010 Hayter
2010/0114026 A1 5/2010 Karratt et al.
2010/0121170 A1 5/2010 Rule
2010/0137784 A1 6/2010 Cefai et al.
2010/0152658 A1 6/2010 Hanson et al.
2010/0174228 A1 7/2010 Buckingham et al.
2010/0211003 A1 8/2010 Sundar et al.
2010/0228110 A1 9/2010 Tsoukalis
2010/0262117 A1 10/2010 Magni et al.
2010/0262434 A1 10/2010 Shaya
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.
2011/0054390 A1 3/2011 Searle et al.
2011/0054399 A1 3/2011 Chong et al.
2011/0098548 A1* 4/2011 Budiman ............... G16H 50/50 600/365
2011/0124996 A1 5/2011 Reinke et al.
2011/0144586 A1 6/2011 Michaud et al.
2011/0160652 A1 6/2011 Yodfat et al.
2011/0178472 A1 7/2011 Cabiri
2011/0190694 A1 8/2011 Lanier, Jr. et al.

(56) References Cited

U.S. PATENT DOCUMENTS

2011/0202005 A1 8/2011 Yodfat et al.
2011/0218495 A1 9/2011 Remde
2011/0230833 A1 9/2011 Landman et al.
2011/0251509 A1 10/2011 Beyhan et al.
2011/0313680 A1 12/2011 Doyle et al.
2011/0316562 A1 12/2011 Cefai et al.
2012/0003935 A1 1/2012 Lydon et al.
2012/0010594 A1 1/2012 Holt et al.
2012/0030393 A1 2/2012 Ganesh et al.
2012/0053556 A1 3/2012 Lee
2012/0078067 A1 3/2012 Kovatchev et al.
2012/0078161 A1 3/2012 Masterson et al.
2012/0078181 A1 3/2012 Smith et al.
2012/0101451 A1 4/2012 Boit et al.
2012/0123234 A1 5/2012 Atlas et al.
2012/0136336 A1* 5/2012 Mastrototaro ..... A61B 5/14532 604/504
2012/0190955 A1 7/2012 Rao et al.
2012/0203085 A1 8/2012 Rebec
2012/0203178 A1 8/2012 Tverskoy
2012/0215087 A1 8/2012 Cobelli et al.
2012/0225134 A1 9/2012 Komorowski
2012/0226259 A1 9/2012 Yodfat et al.
2012/0232520 A1 9/2012 Sloan et al.
2012/0238851 A1 9/2012 Kamen et al.
2012/0271655 A1 10/2012 Knobel et al.
2012/0277668 A1 11/2012 Chawla
2012/0282111 A1 11/2012 Nip et al.
2012/0295550 A1 11/2012 Wilson et al.
2013/0030358 A1 1/2013 Yodfat et al.
2013/0158503 A1 6/2013 Kanderian, Jr. et al.
2013/0178791 A1 7/2013 Javitt
2013/0231642 A1 9/2013 Doyle et al.
2013/0253472 A1 9/2013 Cabiri
2013/0261406 A1 10/2013 Rebec et al.
2013/0296823 A1 11/2013 Melker et al.
2013/0317753 A1 11/2013 Kamen et al.
2013/0338576 A1 12/2013 OConnor et al.
2014/0005633 A1 1/2014 Finan
2014/0066886 A1 3/2014 Roy et al.
2014/0074033 A1 3/2014 Sonderegger et al.
2014/0121635 A1 5/2014 Hayter
2014/0128839 A1 5/2014 Dilanni et al.
2014/0135880 A1 5/2014 Baumgartner et al.
2014/0146202 A1 5/2014 Boss et al.
2014/0180203 A1 6/2014 Budiman et al.
2014/0180240 A1 6/2014 Finan et al.
2014/0200426 A1 7/2014 Taub et al.
2014/0200559 A1 7/2014 Doyle et al.
2014/0230021 A1 8/2014 Birthwhistle et al.
2014/0276554 A1 9/2014 Finan et al.
2014/0276556 A1 9/2014 Saint et al.
2014/0278123 A1 9/2014 Prodhom et al.
2014/0309615 A1 10/2014 Mazlish
2014/0316379 A1 10/2014 Sonderegger et al.
2014/0325065 A1 10/2014 Birtwhistle et al.
2015/0018633 A1 1/2015 Kovachev et al.
2015/0025329 A1 1/2015 Amarasingham et al.
2015/0025495 A1 1/2015 Peyser
2015/0120317 A1 4/2015 Mayou et al.
2015/0134265 A1 5/2015 Kohlbrecher et al.
2015/0165119 A1 6/2015 Palerm et al.
2015/0173674 A1 6/2015 Hayes et al.
2015/0213217 A1 7/2015 Amarasingham et al.
2015/0217052 A1 8/2015 Keenan et al.
2015/0217053 A1 8/2015 Booth et al.
2015/0265767 A1 9/2015 Vazquez et al.
2015/0289823 A1 10/2015 Rack-Gomer et al.
2015/0306314 A1 10/2015 Doyle et al.
2015/0351671 A1 12/2015 Vanslyke et al.
2015/0366945 A1 12/2015 Greene
2016/0015891 A1 1/2016 Papiorek
2016/0038673 A1 2/2016 Morales
2016/0038689 A1 2/2016 Lee et al.
2016/0051749 A1 2/2016 Istoc
2016/0082187 A1 3/2016 Schaible et al.
2016/0089494 A1 3/2016 Guerrini
2016/0175520 A1 6/2016 Palerm et al.
2016/0228641 A1 8/2016 Gescheit et al.
2016/0243318 A1 8/2016 Despa et al.
2016/0256087 A1 9/2016 Doyle et al.
2016/0287512 A1 10/2016 Cooper et al.
2016/0302054 A1 10/2016 Kimura et al.
2016/0331310 A1 11/2016 Kovatchev
2016/0354543 A1 12/2016 Cinar et al.
2017/0049386 A1 2/2017 Abraham et al.
2017/0143899 A1 5/2017 Gondhalekar et al.
2017/0143900 A1 5/2017 Rioux et al.
2017/0156682 A1 6/2017 Doyle et al.
2017/0173261 A1 6/2017 OConnor et al.
2017/0189625 A1 7/2017 Cirillo et al.
2017/0216518 A1 8/2017 Davis et al.
2017/0232195 A1 8/2017 Desborough et al.
2017/0281877 A1 10/2017 Marlin et al.
2017/0296746 A1 10/2017 Chen et al.
2017/0311903 A1 11/2017 Davis et al.
2017/0348482 A1 12/2017 Duke et al.
2018/0036495 A1 2/2018 Searle et al.
2018/0040255 A1 2/2018 Freeman et al.
2018/0075200 A1 3/2018 Davis et al.
2018/0075201 A1 3/2018 Davis et al.
2018/0075202 A1 3/2018 Davis et al.
2018/0092576 A1 4/2018 O'Connor et al.
2018/0126073 A1 5/2018 Wu et al.
2018/0169334 A1 6/2018 Grosman et al.
2018/0200434 A1 7/2018 Mazlish et al.
2018/0200438 A1 7/2018 Mazlish et al.
2018/0200441 A1 7/2018 Desborough et al.
2018/0204636 A1 7/2018 Edwards et al.
2018/0277253 A1 9/2018 Gondhalekar et al.
2018/0289891 A1 10/2018 Finan et al.
2018/0296757 A1 10/2018 Finan et al.
2018/0342317 A1 11/2018 Skirble et al.
2018/0369479 A1 12/2018 Hayter et al.
2019/0030245 A1 1/2019 Baviere et al.
2019/0076600 A1 3/2019 Grosman et al.
2019/0240403 A1 8/2019 Palerm et al.
2019/0290844 A1 9/2019 Monirabbasi et al.
2019/0336683 A1 11/2019 O'Connor et al.
2019/0336684 A1 11/2019 O'Connor et al.
2019/0348157 A1 11/2019 Booth et al.
2020/0046268 A1 2/2020 Patek et al.
2020/0101222 A1 4/2020 Lintereur et al.
2020/0101223 A1 4/2020 Lintereur et al.
2020/0101225 A1 4/2020 O'Connor et al.
2020/0219625 A1 7/2020 Kahlbaugh
2020/0342974 A1 10/2020 Chen et al.
2021/0050085 A1 2/2021 Hayter et al.
2021/0098105 A1 4/2021 Lee et al.
2022/0023536 A1 1/2022 Graham et al.

FOREIGN PATENT DOCUMENTS

CN 1297140 A 5/2001
DE 19756872 A1 7/1999
EP 0341049 A2 11/1989
EP 0496305 A2 7/1992
EP 0549341 A1 6/1993
EP 1491144 A1 12/2004
EP 0801578 B1 7/2006
EP 2139382 A1 1/2010
EP 2397181 A1 12/2011
EP 2666520 A1 11/2013
EP 2695573 A2 2/2014
EP 2830499 A1 2/2015
EP 2943149 A1 11/2015
EP 3177344 A1 6/2017
EP 3314548 A1 5/2018
EP 1571582 B1 4/2019
EP 2897071 B1 5/2019
EP 3607985 A1 2/2020
GB 2443261 A 4/2008
JP 51125993 A 11/1976
JP 02131777 A 5/1990

(56) References Cited

FOREIGN PATENT DOCUMENTS

| | | | |
|---|---|---|---|
| JP | 2004283378 | A | 10/2007 |
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 9800193 | A1 | 1/1998 |
| WO | 9956803 | A1 | 11/1999 |
| WO | 0030705 | A1 | 6/2000 |
| WO | 200032258 | A1 | 6/2000 |
| WO | 0172354 | A2 | 10/2001 |
| WO | 2002015954 | A1 | 2/2002 |
| WO | 2002043866 | A2 | 6/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2004043250 | A1 | 5/2004 |
| WO | 2005110601 | A1 | 5/2004 |
| WO | 2004092715 | A1 | 10/2004 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2007064835 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010053702 | A1 | 5/2010 |
| WO | 2010132077 | A1 | 11/2010 |
| WO | 2010138848 | A1 | 12/2010 |
| WO | 2010147659 | A2 | 12/2010 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2021011738 | A1 | 1/2021 |
| WO | 2021026004 | A1 | 2/2021 |

OTHER PUBLICATIONS

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

"Read NFC Tags with an iPHone App on iOS 11", GoToTags, Sep. 11, 2017, web <https://gototags.com/blog/read-nfc-tags-with-an-iphone-app-on-ios-11/> (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

International Search Report and Written Opinion for Application No. PCT/US2019/030562, Sep. 25, 2019, 19 pages.

International Search Report and Written Opinion for the International Patent Application No. PCT/US2020/052125, mailed Aug. 12, 2020, 15 pages.

(56) References Cited

OTHER PUBLICATIONS

International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16—line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116—line 118, line 439—line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
Anonymous: "Temp-Targets", AndroidAPS documentation, Dec. 30, 2020 (Dec. 30, 2020), pp. 1-3, Retrieved from the Internet: URL:https://github.com/openaps/AndroidAPSdocs/blob/02ebd7c2a79e6691a1d2deflele272cele4ab816/docs/EN/Usage/temptarget.md [retrieved on Dec. 8, 2022].
Jalbert Manon et al: "Glycemic variability indices can be used to diagnose islet transplantation success in type 1 diabetic patients", Acta Diabetologica, Springer Milan, Milan, vol. 57, No. 3, Oct. 10, 2019 (Oct. 10, 2019). pp. 335-345.
Anonymous: "Coefficient of variation", Wikipedia, May 18, 2021 (May 18, 2021), pp. 1-8, Retrieved from the Internet: URL:https://en.wikipedia.org/w/index.php?title=Coefficient_of_variation&oldid=1023881676 [retrieved on Dec. 8, 2022].
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.

(56) References Cited

OTHER PUBLICATIONS

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple,and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

International Search Report and Written Opinion in PCT/US2008/079641 dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et. al.,"Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; Chest/127/5/May 2005.

Glucon Critical Care Blood Glucose Monitor, Glucon; retrieved on Dec. 29, 2010 from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol. Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

(56) References Cited

OTHER PUBLICATIONS

Khodaei et al., “Physiological Closed-Loop Contol (PCLC) Systems: Review of a Modern Frontier in Automation”, IEEE Access, IEEE, USA, vol. 8, Jan. 20, 2020, pp. 23965-24005.
E. Atlas et al., “MD-Logic Artificial Pancreas System: A pilot study in adults with type 1 diabetes”, Diabetes Care, vol. 33, No. 5, Feb. 11, 2010, pp. 1071-1076.

* cited by examiner

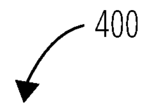

DETERMINE THAT A USER'S BLOOD GLUCOSE MEASUREMENT VALUE IS DIVERGING FROM A TARGET BLOOD GLUCOSE RANGE 402

DETERMINE AN AFTER-INSULIN-ON-BOARD BLOOD GLUCOSE MEASUREMENT VALUE FOR THE USER 404

DETERMINE, USING THE DETERMINED AFTER-INSULIN-ON-BOARD BLOOD GLUCOSE MEASUREMENT VALUE FOR THE USER, AN AMOUNT OF RESCUE CARBOHYDRATES TO BE CONSUMED BY THE USER TO MAINTAIN THE USER'S BLOOD GLUCOSE MEASUREMENT VALUE WITHIN THE TARGET BLOOD GLUCOSE RANGE 406

FIG. 4

ASSESS FACTOR(S) RELATED TO A POTENTIAL IMPENDING HYPOGLYCEMIC EVENT FOR A USER 502

BASED ON A RESULT OF THE ASSESSMENT OF THE FACTOR(S), DETERMINE WHETHER THE USER IS APPROACHING THE POTENTIAL IMPENDING HYPOGLYCEMIC EVENT FOR THE USER 504

IN RESPONSE TO A DETERMINATION THAT THE USER IS APPROACHING THE POTENTIAL IMPENDING HYPOGLYCEMIC EVENT FOR THE USER, DETERMINING A NUMBER OF RESCUE CARBOHYDRATES TO SUGGEST FOR CONSUMPTION BY THE USER 506

FIG. 5

TECHNIQUES FOR RECOMMENDING RESCUE CARBOHYDRATE INGESTION IN AUTOMATIC MEDICATION DELIVERY SYSTEMS

RELATED APPLICATIONS

This application claims the benefit of U.S. Provisional Patent Application No. 63/220,824, filed Jul. 12, 2021, the contents of which are incorporated herein by reference in their entirety.

BACKGROUND

People with T1DM often require ingestion of fast-acting carbohydrates to compensate for a hypoglycemic event. This risk is still present, although with reduced frequency, for AID system users, as users typically still deliver bolus insulin manually, and changes in the user's insulin needs mean automated insulin delivery may also not be the optimal quantity needed for those users.

One of biggest challenges for people living with diabetes can be intaking the appropriate amount of carbohydrates during a hypoglycemic event to return to target blood sugar range.

Often, the user intakes too many carbohydrates in response experiencing symptoms of a hypoglycemic event or to the potential of an impending hypoglycemic event, which will result in hyperglycemia. This affects the individual's overall Time in Range (TIR) (the amount of time spent in range of the target blood sugar (blood glucose) setting), continuous blood glucose monitor (CGM) standard deviation (SD) reading (i.e., the variability of glucose readings) and can result in a higher HbA1c reading due to a large glycemic variability. This is considered a rebound event and the diabetic may experience recurring symptoms of hypoglycemia. The situation is at its worst when the rebound events are occurring frequently during the course of a day because the person is unable to gain control of the delivery of insulin and the ingestion of carbohydrates.

It would be beneficial if a drug delivery system was provided that enabled the user to gain control of the delivery of insulin as well as the consumption of carbohydrates to maximize TIR and keep standard deviation of blood sugar as low as possible.

BRIEF SUMMARY

In one aspect, a drug delivery system is provided that includes a processor and a memory storing instructions that when executed by the processor enable the processor to determine that a blood glucose measurement value of a user is diverging from a target blood glucose range. An after-insulin-on-board blood glucose measurement value is determined for the user. By using the user's blood glucose measurement value, an amount of rescue carbohydrates to be consumed by the user is determined to maintain the user's blood glucose measurement value within the target blood glucose range. The determined amount of the rescue carbohydrates may be output.

In another aspect, a drug delivery system is provided that includes a processor and a memory storing instructions that when executed by the processor enable the processor to assess factors related to a potential impending hypoglycemic event for a user. Based on a result of the assessment of the factors, the processor determines whether the user is approaching the potential impending hypoglycemic event. In response to a determination by the processor that the user is approaching the potential impending hypoglycemic event for the user, a number of rescue carbohydrates to suggest for consumption by the user may be determined.

In a further aspect, a drug delivery system is provided that includes a processor and a memory storing instructions that when executed by the processor enable the processor to monitor a trend of blood glucose measurement values over a series of measurement cycles. The processor, based on the monitored trend, may identify a potential excursion outside a range of a target blood glucose measurement value setting of a user. In response to the identified potential excursion, the processor may generate an alert to the user to consume rescue carbohydrates.

BRIEF DESCRIPTION OF THE DRAWINGS

To easily identify the discussion of any particular element or act, the most significant digit or digits in a reference number refer to the figure number in which that element is first introduced.

FIG. 4 illustrates another example process to determine an amount of rescue carbohydrates for a user according to an aspect of the disclosed subject matter.

FIG. 5 illustrates a process in accordance with an aspect of the disclosed subject matter.

DETAILED DESCRIPTION

Figure 1:
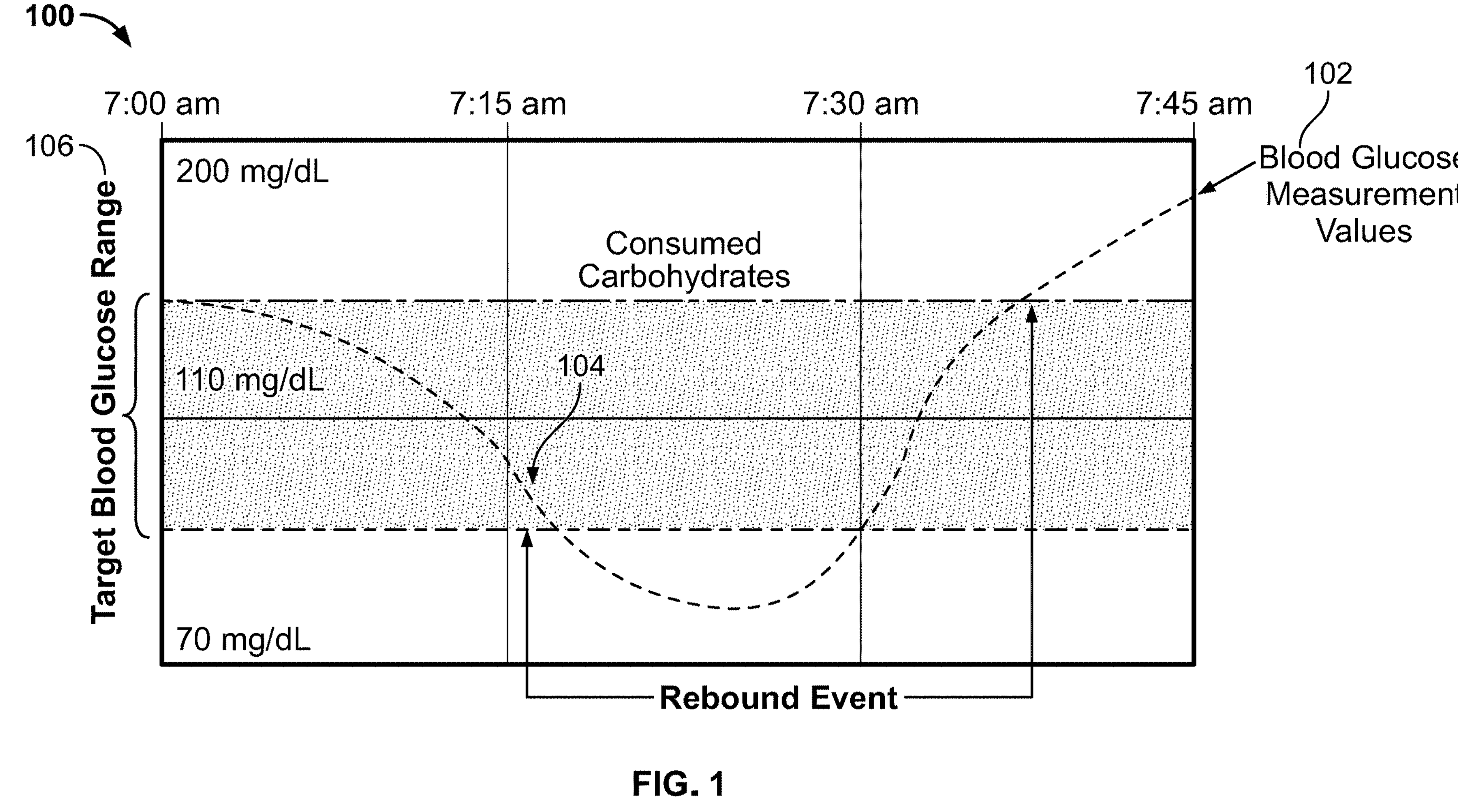
FIG. 1 is a graphic showing blood glucose measurement values in an example of a rebound effect related to the disclosed subject matter.

The following examples provide techniques for AID systems to recommend rescue carbohydrate (CHO) ingestion in advance of the users noticing signs of hypoglycemia themselves, by assessing varying factors such as rate of change (RoC) of glucose, pre-existing insulin-on-board, recency of user bolus, and others.

The disclosed examples provide techniques that may be used with any additional algorithms or computer applications that manage blood glucose levels and insulin therapy. These algorithms and computer applications may be collectively referred to as "medication delivery algorithms" or "medication delivery applications" and may be operable to deliver different categories of drugs (or medications), such as chemotherapy drugs, pain relief drugs, diabetes treatment drugs (e.g., insulin, glucagon and/or glucagon-like peptides), blood pressure medication, or the like.

A type of medication delivery algorithm (MDA) may include an "artificial pancreas" algorithm-based system, or more generally, an artificial pancreas (AP) application. For ease of discussion, the computer programs and computer applications that implement the medication delivery algorithms or applications may be referred to herein as an "AP application." An AP application may be configured to provide automatic delivery of insulin based on signals received from an analyte sensor, such as a continuous blood glucose monitor (CGM), or the like. In an example, the artificial pancreas (AP) application may operate in cooperation with an automatic glucose control (AGC) application or algorithm. The AGC application when executed by a processor may enable monitoring of a user's blood glucose measurement values, determine an appropriate level of insulin for the user based on the monitored glucose values (e.g., blood glucose concentrations or blood glucose measurement values) and other information. The AGC application may be operable to maintain a user's blood glucose levels in range of a target blood glucose setting. The "target blood glucose setting" may be a setting that the AGC uses as an optimal blood glucose measurement value and performs different functions to maintain the user's blood glucose as close as possible to the setting. For example, a target blood glucose measurement value setting may be a value that falls within the range of 80 mg/dL to 120 mg/dL, which is a range satisfying a clinical standard of care for treatment of diabetes. Other ranges may be used such as 70 mg/dL to 120 mg/dL or 70 mg/dL to 150 mg/dL. The target blood glucose measurement value setting may be 100 mg/dL, which is median value of the foregoing range. Of course, other values such as 110 mg/dL may be selected as the user's target blood glucose measurement value setting with a corresponding plus or minus tolerance, such as 5% or 10% to establish a range of values (e.g., 104.5 mg/dL to 115.5 mg/dL, if the tolerance is 5%). In addition, an AGC application as described herein may be operable to determine when a user's blood glucose is getting into the hypoglycemic range or the hyperglycemic range.

When maintaining the user's blood glucose measurement values within range, the AGC algorithm may be operable to monitor the standard deviation of the blood glucose measurement values from the target blood glucose measurement value setting. The standard deviation (SD) may also be compared to a target SD. The SD target is typically set to be as low as possible. A Coefficient of Variation (CV) (which equals (SD/average glucose reading)), and the CV goal target may be approximately less than or equal to 36% (e.g., CV≤36%).

Coefficient of variation and standard deviation, which are the values that reflect how well the user's blood glucose measurement values are within the target blood glucose range. A lower value for the coefficient of variation and standard deviation mean the blood glucose measurement value is within range, while a higher value for the coefficient of variation and standard deviation means the user's blood glucose measurement values are not remaining within the target blood glucose range.

FIG. 1 is a graphic showing blood glucose measurement values in an example of a rebound effect related to the disclosed subject matter. The occurrence of the example rebound event is addressed in the examples of FIG. 2 to FIG. 7. As shown in graphic 100, the blood glucose measurement values 102 of the user are shown by the dotted line that begins at 7 am and within the user's target blood glucose range 106, which is centered around a target blood glucose measurement value setting of 110 mg/dL. Of course, the target blood glucose measurement value setting and the target blood glucose range may vary over time or from user to user.

As time passes, the user's blood glucose measurement values are trending downward (i.e., have a negative rate of change). As shown in FIG. 1, a brief time after 7:15 am, the user's blood glucose measurement values are outside the target blood glucose range 106 (i.e., below the lower tolerance for the target blood glucose range), and potentially heading to a blood glucose measurement value at which the user is experiencing symptoms of hypoglycemia. At this time, the user may ingest carbohydrates (shown as consumed carbohydrates 104) to increase their blood glucose measurement value. It may take some time for the consumed carbohydrates 104 to counteract the negative rate of change of the user's blood glucose measurement values. As shown at approximately 7:30 am, the user's blood glucose measurement values are beginning to trend upwards. The amount of consumed carbohydrates may be unspecified, or merely be a snack that is readily accessible to the user. But in the FIG. 1 example, the amount of carbohydrates may have been too much as evidenced by the steep trend of the user's blood glucose measurement values (i.e., the rate of change is high in the positive direction) and the user's blood glucose measurement values are again heading out of the target blood glucose range 106. This is another rebound event but the trend in the user's blood glucose measurement values is in the direction of a potential hyperglycemic event. In response to the potential hyperglycemic event due to the excess carbohydrates consumed by the user, the user may need to increase the amount of insulin to be delivered using either a micro-bolus or a rescue bolus to reduce the effects of the excess carbohydrates.

It would be beneficial if the automatic drug delivery system were operable to recommend carbohydrate ingestion in advance of the users noticing signs of hypoglycemia themselves, by assessing varying factors such as rate of change (RoC) of glucose, pre-existing insulin-on-board, how recently has the user delivered a bolus (i.e., recency of user bolus), and/or other factors. Examples of techniques for determining whether actions need to be taken to address a potential impending hypoglycemic event are explained with reference to the following examples.

Figure 2:
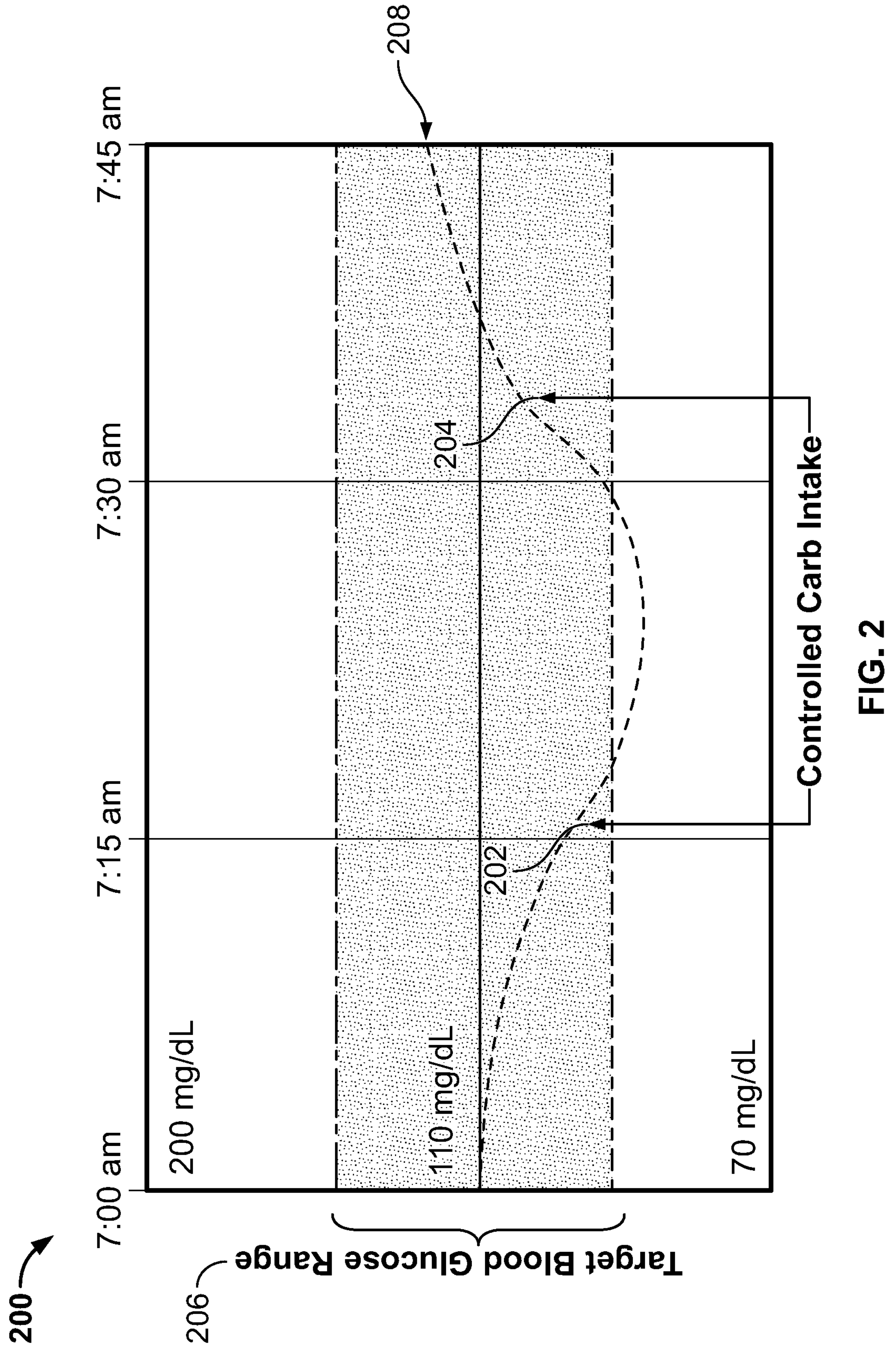
FIG. 2 is a graphic showing blood glucose measurement values in an example response to counteract a rebound effect as described in the disclosed subject matter.

FIG. 2 is a graphic illustrating a benefit of the presently disclosed subject matter. The target blood glucose measurement value setting may be 110 mg/dL and the target blood glucose range 206, which are the same as in the graphic 100 of FIG. 1. However, in the graphic 200, the blood glucose measurement values 208 shown in FIG. 2 remain substantially within the target blood glucose range 206 and with lesser excursion from the target blood glucose measurement value setting than in the graphic 100 of FIG. 1. Using the processes described herein, the user may receive a recommendation to consume an amount of rescue carbohydrates determined using the processes described herein for controlled carbohydrate intake, and may consume the carbohydrates at multiple times, such as intake 202 and intake 204. As such, the user, when using the described techniques and devices, may advantageously remain within range of their target blood glucose measurement value setting for a greater duration.

The example processes illustrated in and explained with reference to FIGS. 3-7 relate to an AGC application being operable to determine how many carbohydrates a user needs based on the amount of insulin-on-board to address a potential impending hypoglycemic event. The number of determined carbohydrates is approximately the minimum amount of carbohydrates (also referred to as "rescue carbohydrates") that return the user's blood glucose measurement values back to within range of the user's target blood glucose measurement value setting.

The following examples provide a solution that controls the rebound events and any potential impending hypoglycemic events associated with the rebound events by an automatic medication delivery system. Examples of processes for determining whether rescue carbohydrates are needed are described with reference to FIG. 3 and FIG. 4. The disclosed techniques may potentially reduce the chance of a hyperglycemic rebound event and reduce overall SD for the user as shown in FIG. 2. An advantage of the disclosed techniques and systems being that users may have reduced HbA1c measurements as well as a reduced likelihood of hypoglycemic and hyperglycemic events.

Figure 3:
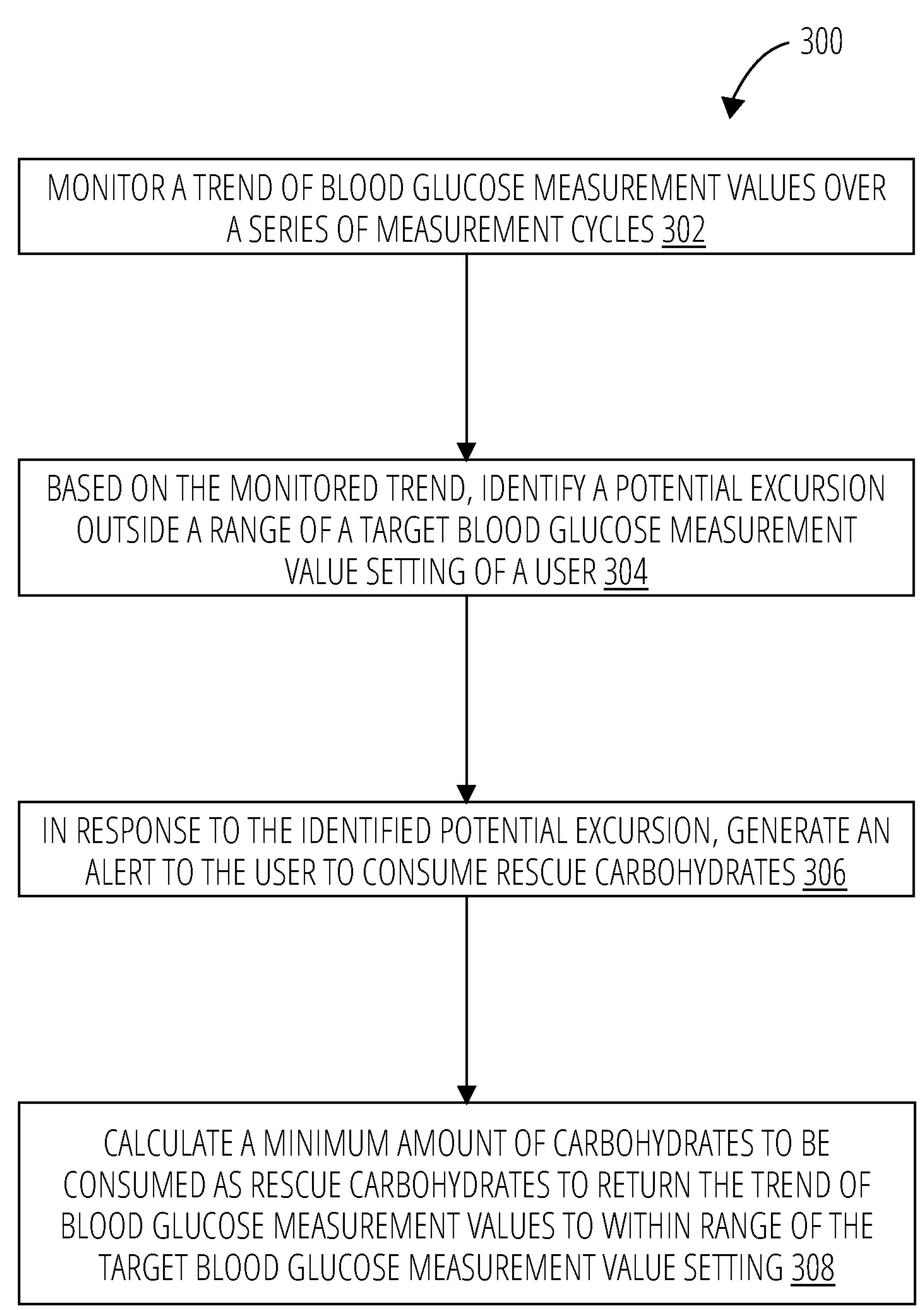
FIG. 3 illustrates a process example for generating an alert that rescue carbohydrates may be needed by a user according to an aspect of the disclosed subject matter.

FIG. 3 illustrates an exemplary process for generating an alert to a device of the user that rescue carbohydrates may be needed. In the example process, a processor may be configured to, or be operable to, perform different functions and be coupled to an analyte sensor, a controller and/or a wearable drug delivery device. The process 300 is an example of a process that addresses the problem of recurring rebound events and provides the advantage of enabling the user to spend a greater amount of time within range of the user's target blood glucose measurement value setting.

In block 302 of process 300, the processor executing an AGC application or algorithm may monitor a trend of blood glucose measurement values over a series of measurement cycles. A measurement cycle may be a preset period of time, such as 5 minutes, 1 minute, 10 minutes, or 15 minutes. In some instances, the preset periods of time for the measurement cycle may be varied during the course of a day, or a week (e.g., Monday may have a first measurement cycle while Friday may have a second, different measurement cycle).

In block 304, the processor when implementing the process 300 may, based on the monitored trend, identify a potential excursion of the user's blood glucose measurement values outside a range of a target blood glucose measurement value setting of a user. In an example, the processor may identify the potential excursion by determining a standard deviation of a blood glucose measurement value from the target blood glucose measurement value setting. The processor may be operable to determine a coefficient of variation and compare the coefficient of variation to a variation threshold. The variation threshold may, for example, be a selected percentage of a target standard deviation, such as 12%, 36%, or the like. The processor, in response to the coefficient of variation exceeding the variation threshold, may output a control signal for generating the alert.

In block 306, process 300 may enable the processor to generate an alert to the user to consume rescue carbohydrates in response to the identified potential excursion. The processor may operate to output a prompt to consume the rescue carbohydrates on a graphical user interface of a user device as the alert.

The processor, in block 308, may be further operable to calculate a minimum amount of carbohydrates to be consumed as rescue carbohydrates that is expected to reverse the trend of blood glucose measurement values and return the user's blood glucose measurement value to within the range of the target blood glucose measurement value setting of the user. The processor may use various methods of determining the minimum amount of carbohydrates to recommend as rescue carbohydrates. In addition, or alternatively, the processor may use various methods of determining the maximum amount of carbohydrates to recommend as rescue carbohydrates. An example method for determining rescue carbohydrates is described below with reference to FIG. 6.

Other technical features may be readily apparent to one skilled in the art from the following figures, descriptions, and claims.

FIG. 4 illustrates another example of a process for determining whether an alert that rescue carbohydrates may be needed to be generated. In the example of FIG. 4, the amount of insulin-on-board (IOB) may be considered when determining whether to recommend rescue carbohydrates for consumption. In the examples, IOB may refer to an amount of insulin that a user has in their body that has not yet been metabolized. The processor implementing the various process examples of FIGS. 3-6 may be operable to evaluate a number of factors that may be used in the determination of whether to recommend rescue carbohydrates.

The process 400 at block 402 may determine that a user's blood glucose measurement value is diverging from a target blood glucose range. The user's blood glucose measurement value may be considered to be diverging from the target blood glucose range when the user's blood glucose measurement values are trending lower (e.g., decreased 10% after a set period of time, such as 90 minutes) or has a negative rate of change in the direction of a hypoglycemic threshold. In response to the determination that the user's blood glucose measurement value is diverging from a target blood glucose range, the process 400 may proceed to block 404.

In block 404, the process 400 determines an after-IOB blood glucose measurement value using an amount of IOB for the user. The "after-IOB blood glucose measurement value" may, for example, be a blood glucose measurement value that takes in account a current, or most recent, IOB amount at a particular time as explained below. In one example, the user's IOB may be calculated by a processor summing an amount of insulin delivered over an immediate period of time, such as 90 minutes, and utilizing a correction factor to account for how effectively a user's body metabolizes insulin delivered with the immediate period of time. This example may be expressed mathematically as shown in Equation 1 below.

The outcome of the Equation 1 may be used to determine the after-insulin-on-board blood glucose measurement value $G_{afteriob}$ for the user. In Equation 1, G(i) is the user's blood glucose measurement value at a particular time (i), IOB(i) is the user's insulin-on-board at the particular time (i), and CF(i) is the user's correction factor at particular time (i), in Equation 1:

$$G_{afteriob} = G(i) - IOB(i) \cdot CF(i) \qquad \text{Eq. 1}$$

For example, the processor when evaluating Equation 1 may further receive from an analyte sensor a present blood glucose measurement value of the user which is used in Equation 1. The particular time (i) may be the present time or may be a time associated with receipt of a last blood glucose measurement value from an analyte sensor (e.g., a previous cycle at time (i–3 minutes) or the like.

As an alternative to receiving the blood glucose measurement value from the analyte sensor, the processor may be operable to estimate a value of the user's blood glucose measurement value using a blood glucose measurement value from a user history of blood glucose measurement value and other values, such as insulin delivery dates and times and amounts.

The processor may also be able to determine from historical data of the user the values of IOB(i) and CF(i). In such an alternative, the processor may be operable to calculate or estimate each of G(i), IOB(i) and CF(i) at the particular time (i) using prior values based on information stored in user history data in a memory or available via cloud-based services. These estimated values of G(i), IOB(i) and CF(i) may be used in Equation 1 to determine $G_{afteriob}$ using Equation 1 as outlined above.

In an operational example, a user's current blood glucose measurement value is 100 mg/dL which places the user's blood glucose measurement value at approximately 30 mg/dL from the user's hypoglycemic threshold. In the example, the user's insulin-to-carbohydrate ratio is 1-to-30, meaning 1 Unit (U) of insulin processes 30 grams of carbohydrates. If the user's IOB is less than 1 U, the user may potentially begin experiencing symptoms of hypoglycemia within a short period of time (i.e., begin experiencing a hypoglycemic event). In response to determining the user's IOB is less than 1 U, the process 400 may proceed to block 406.

In another operational example, a user may have an IOB of 0 (zero) Units (U), and the user may ingest a meal and have delivered a bolus of 3 U of insulin. After delivering the bolus of 3 U of insulin, the user's IOB is 3 U and the user's blood glucose measurement value is 100 mg/dL. In this example, the system may determine that an alert is unnecessary in response to these user conditions, but may determine to wait for a period of time to pass, or until the user's blood glucose measurement value is closer to the hypoglycemic threshold (40-70 mg/dL) before determining to deliver an alert.

In block 406, the processor implementing process 400 may determine, using the determined after-IOB blood glucose measurement value, an amount of rescue carbohydrates to be consumed by the user to maintain the user's blood glucose measurement value within the target blood glucose range. There may be numerous techniques for determining the amount of rescue carbohydrates to recommend to the user to enable the user's blood glucose measurement value to return to within range of the target blood glucose measurement value setting, such as the example illustrated in and described with reference to FIG. 6.

In some situations, such as immediately after a bolus, the system may have a setting not to generate an alert for the user to have a rescue carbohydrate because the delivery of the bolus may be due to the consumption of a meal, snack, or the like.

Other technical features may be readily apparent to one skilled in the art from the following figures, descriptions, and claims.

FIG. 5 illustrates example of evaluating a factor or factors for determining whether rescue carbohydrates are to be recommended for a user.

In block 502, process 500 assesses factors related to a potential impending hypoglycemic event for a user. A need for action in response to a potential impending hypoglycemic event can be determined by assessing one or more of several contributing factors. For example, the number of factors to be assessed may be four, or one of four, or the like. Examples of the factors may be 1) a user's blood glucose measurement value may be below a tunable, preset threshold; 2) the outcome of the Equation 1 described above in the example of FIG. 4 being below the minimum blood glucose value; 3) a rate of change of the user's blood glucose measurement values being negative or trending lower (or downward) or exceeding a threshold; and/or 4) a projected blood glucose measurement value being below the minimum blood glucose value.

In an example of a factor being the user's blood glucose measurement value being below a tunable, preset threshold, the processor may evaluate the user's blood glucose measurement value. In the example, the processor may receive a user's blood glucose measurement value from the analyte sensor at a particular time. Alternatively, or additionally, the processor may access a memory or cloud-based service to obtain a past (e.g., prior to the particular time or a present time) blood glucose measurement value. In yet another alternative, the processor may access a memory or cloud-based service and obtain several past blood glucose measurement values and make an estimate of a current or present blood glucose measurement value. Using any one of the blood glucose measurement values, whether received from the analyte sensor, obtained from the memory or the cloud-based services, or the estimated value, the processor may compare the blood glucose measurement value to a tunable blood glucose setting, such as 100 mg/dL, or the like. The tunable blood glucose setting may be set based on a user's experience with symptoms of hypoglycemia. For example, most user's may begin to experience some symptoms of hypoglycemia when their blood glucose measurement value is approximately 100 mg/dL, while other users may experience symptoms at blood glucose measurement values that are higher or lower than 100 mg/dL. Based on the individual user's tolerance for a low blood glucose measurement value, the tunable blood glucose setting may be set accordingly. The processor may proceed to block 504 to evaluate the result to the assessment (i.e., the comparison).

Another alternative of a factor that may be assessed in block 502 may be an implementation in which the processor uses blood glucose measurement value at the particular time (i) and a correction factor as described above with reference to FIG. 4.

As for yet another example, the processor may determine a rate of change or a trend of the user's blood glucose measurement values. In this factor, the rate of change of the user's glucose may be determined to be negative, which means trending downward in value. For example, the processor may further be operable to receive a present blood glucose measurement value of the user from an analyte sensor at predetermined cycle times, such as every 5 minutes. For example, the cycle may be represented by the variable h. The variable h may be incremented with every cycle, and each value of h may have a corresponding blood glucose measurement value. For example, h may equal 1 and the user's blood glucose measurement value may be 120 mg/dL, when h is 2, the user's blood glucose measurement value may be 115 mg/dL, and at h equals 3, the user's blood glucose measurement value may be 109 mg/dL. With the user's blood glucose measurement value decreasing with each cycle, the processor determines that the user's blood glucose measurement value is trending downward or has a negative rate of change, and that rate of change, or slope, may be determined and compared to a threshold value. In the event a negative rate of change is detected, or the quantity of the rate of change exceeds a threshold, actions may be taken as described herein.

In the example, the processor may obtain, from a memory, blood glucose measurement values received over a time period prior to receiving the user's present blood glucose measurement value (i.e., h=3). For example, the blood glucose measurement values at cycles 1 and 2 may have previously been stored in the memory, for example, at the time of receipt from the analyte sensor. After accessing the memory, the processor may retrieve the blood glucose measurement values corresponding to cycles 1 and 2 from the memory. The processor, using the user's present blood glucose measurement value and the blood glucose measurement values obtained from the memory, may determine the rate of change of the blood glucose measurement values. In response to when the rate of change is negative, the processor, at block 506, may use the rate of change in the determination of the number of rescue carbohydrates to suggest to the user to consume to mitigate symptoms of the potential impending hypoglycemic event.

In yet another example of a factor, the processor may evaluate a user's projected blood glucose measurement value with respect to a minimum blood glucose value, where the value of the user's projected blood glucose measurement value is the factor. In the example, the minimum blood glucose value may be 54 mg/dL or the like. When evaluating the user's projected blood glucose measurement value, the processor may use the following equation, Equation 2:

$$G_{afterROC} = G(i) - X(G(i-Y) - G(i)) \quad \text{Eq. 2}$$

where G(i) is the user's blood glucose measurement value at a particular time (i), Y may be a value from 1-6, and X may be a value based on 6/Y.

In an example, the processor may evaluate Equation 2. For example, the processor may further receive a present blood glucose measurement value of the user at time i. For the example, the variable Y may be 3 in which case, X is 6/3 or 2, the G(i) may be 120 mg/dL and i may be 7. Using these values, Equation 2 may be: $G_{afterROC}$=120−2(G(7−3)−120). The processor may evaluate G(7−3) as G(4), which, in this case, the value 4 may represent a prior time, and the blood glucose measurement value stored in the memory that corresponds to the prior time 4 may be, for example, 160 mg/dL. The processor using these values in Equation 2 to calculate $G_{afterROC}$. For example, the processor using the 160 mg/dL retrieved from the memory may determine that $G_{afterROC}$ equals 40 (i.e., $G_{afterROC}$=(120−2(160−120))=(120−2(40))=(120−(80))=40). The value of $G_{afterROC}$ (i.e., 40) may be evaluated against the minimum blood glucose value, which, in this example, may be 54 mg/dL. Based on the outcome of the evaluation (which may be a comparison), the processor may proceed to block 506 to take additional action.

In an example, the processor does not generate a recommendation for rescue carbohydrates unless the user's projected blood glucose measurement value in the next 30 minutes (e.g., h=6 for 6 cycles of measurements, where each cycle occurs every 5 minutes, by an analyte sensor) as calculated using Equation 2 is below, for example, 54 mg/dL. Other threshold values of projected blood glucose measurement values may be used.

In one embodiment, the output of all of the above factors have to indicate a need for the processor to take action, such as generating a recommendation for rescue carbohydrates, to address the potential impending hypoglycemic event. For example, in response to all of the factors indicating that that the user's present blood glucose measurement value is below the hypoglycemic threshold, the calculated value of the user's blood glucose and the projected blood glucose measurement value are both equal to or below the minimum blood glucose value, and the rate of change is negative, the processor operates to generate a signal to use at least one of the four factors in the determination of the number of rescue carbohydrates to suggest.

After assessing the factors, the processor may be operable to evaluate the result of the assessment of each factor. The processor may take action when the result of the assessment of any one of the factors indicating that the user's present blood glucose measurement value is below the hypoglycemic threshold, the calculated value of the user's blood glucose and the projected blood glucose measurement value are both equal to or below the minimum blood glucose value, or the rate of change is negative.

Alternatively, in another embodiment, a plurality, or in another embodiment just one, factor needs to be met to recommend action for impending hypoglycemia. For example, the processor may be operable to select at least one of the four factors in which the user's present blood glucose measurement value is below the hypoglycemic threshold, the calculated value of the user's blood glucose and the projected blood glucose measurement value are both equal to or below the minimum blood glucose value, or the rate of change is negative in the determination of the number of rescue carbohydrates to suggest. For example, based on previous history, the processor may determine the rate of change has been the more reliable indicator (based on a confidence calculation or the like) of the user's progression toward a potential impending hypoglycemic event.

In a further progression of the algorithms, the processor executing the MDA/AGC algorithms or applications may determine which of these contributing factors 1-4 is the most relevant for a particular user, and weigh each of the contributing factors accordingly.

In block 504, process 500 based on a result of the assessment of the factors, the processor determines whether the user is approaching the potential impending hypoglycemic event for the user.

The processor may determine whether other conditions may affect the impact of the potential impending hypoglycemic event, such as the effect of a bolus or an upcoming scheduled and consistent meal time, when determining what action to take in response to the assessment of at least one of the factors. For example, the processor may be operable to determine how recent a bolus was given by determining that the calculated IOB is larger than a typical threshold value. If the bolus was given within a preset period of time, such as within the last 30 minutes, the system may not generate an alert and may return to assessing factors at block 502. Or, if the scheduled and consistently-taken mealtime is within the next 15-20 minutes, the processor may determine that rescue carbohydrates do not need to be recommended at this time. In an operational example, users have varying preferences for pre-bolusing for a meal. Users also have different blood glucose target settings for different meals or snacks at which the user prefers their blood glucose to meet prior to the user eating. For example, the user may have a blood glucose target setting of 90 mg/dL before eating their breakfast. With this user experience in mind, the disclosed system may allow the user to either set such variables with rescue carbohydrates or mute/snooze any alarms or notifications around typical meal times for the user for a set period of time, such as 30 minutes or the like.

In block 506, processor may, in response to a determination that the user is approaching the potential impending hypoglycemic event for the user, determine a number of rescue carbohydrates to suggest for consumption by the user. The processor may use a process such as that described with reference to the example of FIG. 6 to make the determination of the number of rescue carbohydrates to suggest for consumption by the user to mitigate the symptoms the user experiences to the potential impending hypoglycemic event.

Other technical features may be readily apparent to one skilled in the art from the following figures, descriptions, and claims.

Once the need for action is detected, the following potential recommendations and actions can be taken. In the example, the AGC algorithm or application may utilize different functions or equations to determine the amount of rescue carbohydrates to recommend to the user. One action may be to inform the user of the potential impending hypoglycemic event using an audible and/or visual notice.

In an alternative, the system may not make a recommendation of rescue carbohydrates, but may instead recommend that the user should activate HypoProtect Mode, or any other mode within the system that reduces or, even ceases, automated insulin delivery, for, for example, 90 minutes or another time, or until the user's glucose concentration returns above target. The duration of the hold (i.e., the 90 minutes or other time) may be tunable.

Figure 6:
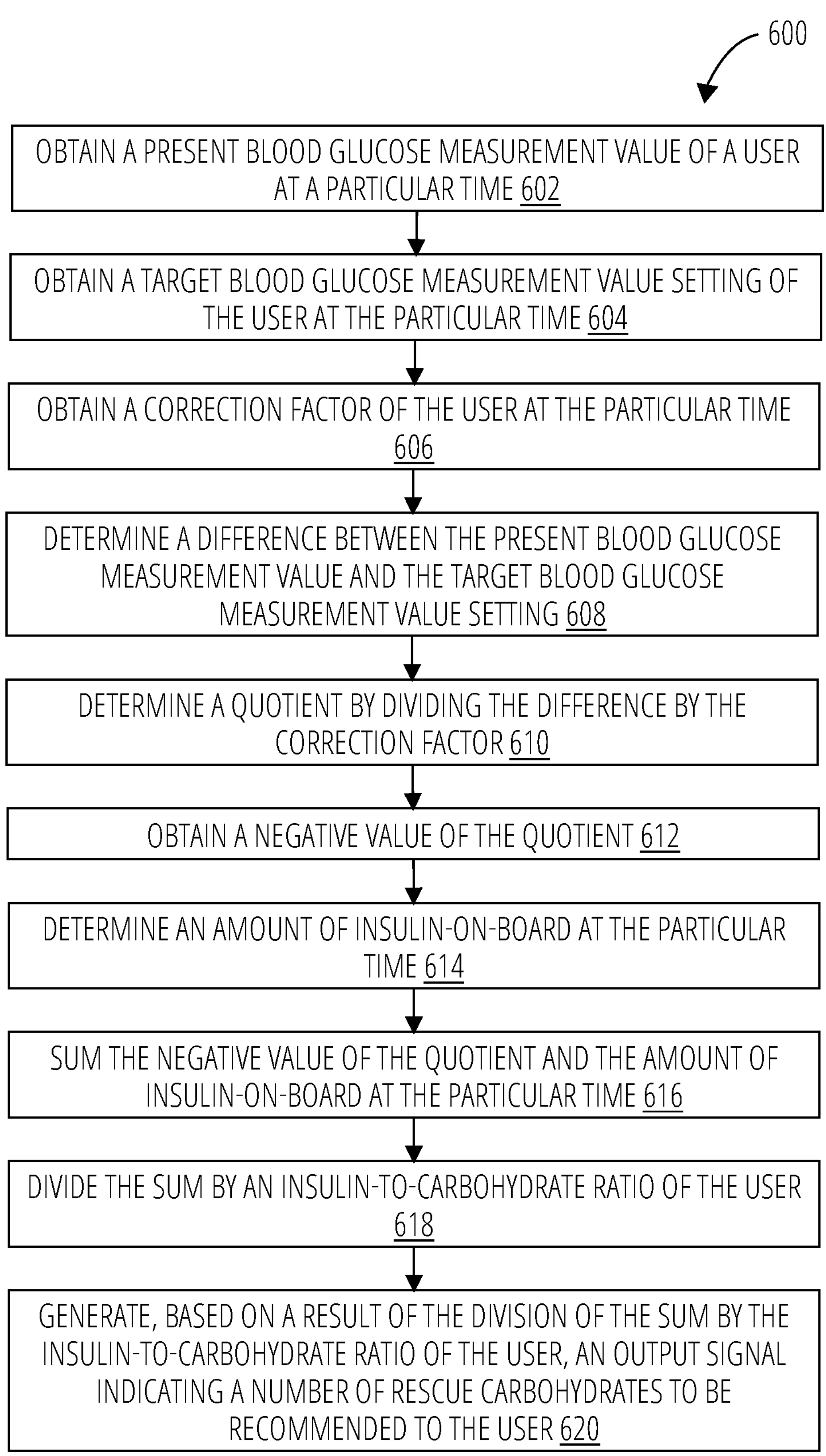
FIG. 6 illustrates a process usable to determine an amount of rescue carbohydrates to recommend to a user in accordance with an aspect of the disclosed subject matter.

For example, the processor may determine to recommend a default value of rescue carbohydrates, such as a nominal amount (e.g., 15 g), which may be tunable. FIG. 6 illustrates a process usable to determine an amount of rescue carbohydrates to recommend to a user in accordance with an aspect of the disclosed subject matter.

Process 600 of FIG. 6 is an example of an equation that may be used by a processor to calculate the amount of rescue carbohydrates for a particular user based on the user's JOB.

In the example, the amount of rescue carbohydrates ($CHO_{rec}$) in grams may be based on the user's current blood glucose measurement value and the user's JOB. Using these two values, the processor is operable to determine a recommended amount of rescue carbohydrates based on the following equation, where SP(i) is the current target blood glucose measurement value setting (i.e., setpoint) at the particular time (i), and IC(i) is the user's current insulin-to-carbohydrate ratio at the particular time (i), G(i) is the user's blood glucose measurement value at the particular time (i), IOB(i) is the insulin-on-board at the particular time (i) and CF(i) is the user's correction factor at particular time (i), in the following equation, Equation 3:

$$CHO_{rec} = \left(-\frac{(G(i) - SP(i))}{CF(i)} + IOB(i)\right)(1/IC(i)) \quad \text{Eq. 3}$$

In block 602, process 600 obtains a present blood glucose measurement value (G) of a user at a particular time (G(i)).

In block 604, process 600 obtains a target blood glucose measurement value setting of the user at the particular time (SP(i)).

In block 606, process 600 obtains a correction factor of the user at the particular time (CF(i)).

In block 608, process 600 determines a difference between the present blood glucose measurement value and the target blood glucose measurement value setting (G(i)–SP(i)).

In block 610, process 600 determines a quotient by dividing the difference (G(i)–SP(i)) by the correction factor (CF(i)).

In block 612, process 600 obtains a negative value of the quotient.

In block 614, process 600 determines an amount of insulin-on-board at the particular time (IOB(i)).

In block 616, process 600 sums the negative value of the quotient and the amount of insulin-on-board at the particular time (IOB(i)).

In block 618, process 600 divides the sum by an insulin-to-carbohydrate ratio of the user. Shown as 1 over (IC(i)) for ease of illustration and explanation. The step at block 618 may also be said as multiplying the quotient by 1 over (IC(i)) (i.e., the inverse of IC(i)).

In block 620, process 600 generates, based on a result of the division of the sum by the insulin-to-carbohydrate ratio of the user, an output signal indicating the number of rescue carbohydrates that is the output of the equation may be presented as a recommendation to the user.

The foregoing processes 300, 400, 500 and 600 may adapt over time. For example, the sensitivity of detection via the various tunable parameters, and the degree of compensation recommended, can both be adjusted over time based on the response of the user. For example, the MDA/AGC algorithm or application may be operable to perform different functions in response to evaluating the different factors related to determining whether a user is about to experience a potential impending hypoglycemic event. For example, the processor may adapt to react differently, if the user confirms the alert within a period of time, such as 5 or 6 minutes, but the user still experiences hypoglycemia within 30 minutes (tunable) after the alert, the processor may incrementally modify the tunable parameters by 10% (tunable, 5-15%), up to 30% of the original value (tunable; 20-50%), towards increased frequency and degree of recommendations, such as transitioning from not recommending rescue carbohydrates to making a recommendation of rescue carbohydrates.

Alternatively, if the user does not confirm the alert within the period of time (e.g., 5 or 6 minutes), and dismisses it later, and the user's glucose concentration still remains above the hypoglycemic threshold (70 mg/dL; tunable), the processor may incrementally modify the tunable parameters by 10% (tunable, 5-15%) up to 30% of original value, towards reduced frequency of recommendations.

Figure 7:
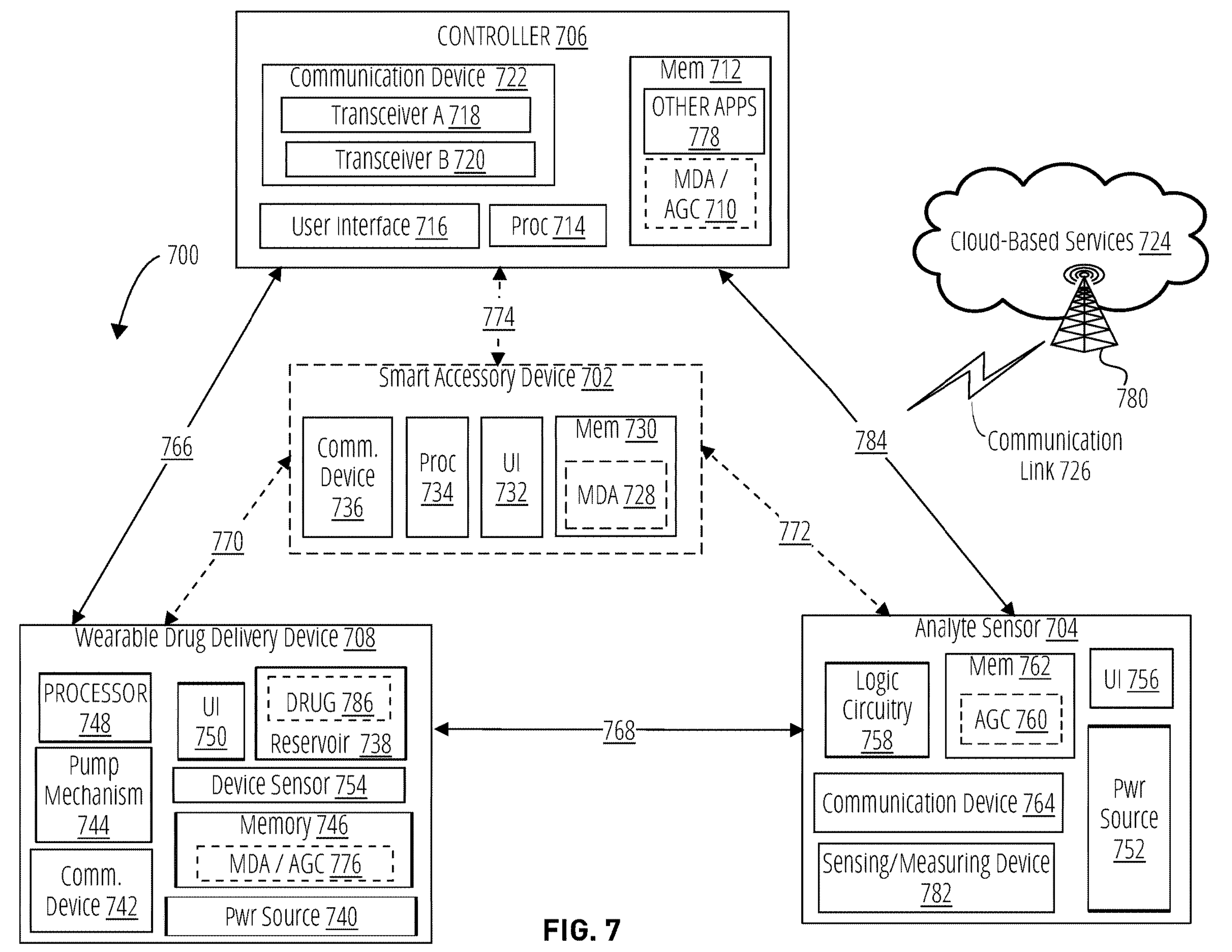
FIG. 7 illustrates a functional block diagram of a system example suitable for implementing the example processes and techniques described herein.

FIG. 7 illustrates a functional block diagram of a system example suitable for implementing the example processes and techniques described herein.

The automatic wearable drug delivery system 700 may implement (and/or provide functionality for) a medication delivery algorithm (MDA), such as an artificial pancreas (AP) application or an automatic glucose control (AGC) application, to govern or control automated delivery of a drug, a therapeutic, or a medication, such as insulin, to a user (e.g., to maintain euglycemia—a normal level of glucose in the blood). The automatic wearable drug delivery system 700 may, for example, include an analyte sensor 704, a controller 706, a wearable drug delivery device 708, and an optional smart accessory device 702.

The controller 706 may be remote from the wearable drug delivery device 708 and may include a user interface 716, a communication device 722, a memory 712, and a processor 714. The user interface 716 is coupled to the processor 714 and operable to receive inputs related to a physiological condition of a user and provide the input to the processor 714. In an example, the input may be a request for a bolus dosage. The controller 706 may include a user interface 716, which may be a keypad, a touchscreen display, levers, light-emitting diodes, buttons on the controller 706, a microphone, and a camera. The user interface 716 may provide inputs, such as a voice input, a gesture (e.g., hand or facial) input to a camera, swipes to a touchscreen, or the like, to processor 714 that, via execution of the programming code, the processor 714 interprets. The user interface 716 may also include output devices, such as a speaker, a display, or the like, and also be configured to allow the processor 714 of the controller 706 to output information (e.g., alarm signals, prompts including as the recommendations for confirming alerts related to potential impending hypoglycemic events, the recommendation of ingesting rescue carbohydrates and the amount of rescue carbohydrates, and the like) for presentation to the user.

The controller 706 may be a computing device such as a smart phone, a tablet, a personal diabetes controller, a dedicated diabetes therapy controller, or the like. In an example, the controller 706 may include a processor 714, a controller memory 712, a user interface 716, and a communication device 722. The controller 706 may contain analog and/or digital circuitry that may be implemented as a processor 714 for executing processes based on programming code stored in the controller memory 712, such as the medication delivery algorithm or application or an automatic glucose control application (MDA/AGC) 710, other apps 778, and related programming code as well as sampling threshold values. The processor 748 may be used to program, adjust settings, and/or control operation of the wearable drug delivery device 708 and/or the analyte sensor 704 as well as the optional smart accessory device 702.

In an operational example, the MDA/AGC 710 may be operable to cause the processor 714 to calculate the amount of rescue carbohydrates. In the operational example, the processor 714 may implement one or more of processes 300, 400 or 500 and may determine that rescue carbohydrates are appropriate. In response, the processor 714 may receive the user's blood glucose measurement value at a particular time from the analyte sensor 704 and obtain from memory 712 a target blood glucose measurement value setting for the user at the particular time. The MDA/AGC 710 may be operable to determine a difference between the user's blood glucose measurement value at the particular time and the target blood glucose measurement value setting for the user at the particular time. The processor 714 may determine an amount of insulin-on-board. The processor 714 may divide the difference by a correction factor of the user to obtain a modified difference value. The processor 714 may take a negative of the modified difference value, sum the negative of the modified difference value with the determined amount of insulin-on-board. The sum may be divided by an insulin-to-carbohydrate ratio of the user to obtain an amount of the rescue carbohydrates to be recommended to the user. The amount of rescue carbohydrates may be presented to the user via the user interface 716.

In another operational example, regardless of the determined amount of rescue carbohydrates, the system 700 may have a default amount of rescue carbohydrates, such as 15 grams, that are to be recommended to the user to be consumed. The default amount of rescue carbohydrates may be factored in for future deliveries of insulin, both basal delivery and bolus delivery. The default amount of rescue carbohydrates may be tunable by the user or clinician based on a user's blood glucose measurement value history, insulin delivery history, time of day and other considerations, such as intensity of physical activity at the particular time, an approximate time until a usual meal time, or the like.

The one or more transceivers, transceiver A 618 and transceiver B 620 may operate according to one or more radio-frequency protocols. In the example, the transceivers 718 and 620 may be a cellular transceiver and a Bluetooth® transceiver, respectively. For example, the transceiver A 718 or transceiver B 720 may be configured to receive and transmit signals containing information usable by the MDA/AGC 710.

The wearable drug delivery device 708 may include processor 748, a reservoir 738, a communication device 742, a power source 740, a memory 746, device sensor 754, user interface (UI) 750, and a pump mechanism 744. The processor 748 may be operable to control the drug delivery device. The reservoir 738 may be configured to contain a liquid drug. The communication device 742 may be coupled to the processor 748. The pump mechanism 744 may be responsive to the processor 748 and fluidically coupled to the reservoir 738.

The memory 746 may store programming code executable by the processor 748. The programming code, for example, may enable the processor 714 to control expelling insulin from the reservoir 738 in response to control signals from the controller 706 and MDA/AGC 610 or based on signals from the optional MDA/AGC 776.

In the example, the communication device 742, which may be a receiver, a transmitter, or a transceiver or other circuitry that operates according to one or more radio-frequency protocols, such as Bluetooth, Wi-Fi, a near-field communication standard, a cellular standard, or the like. The communication device 742 may enable the processor 748 to communicate with the controller 706 and the analyte sensor 704.

The wearable drug delivery device 708 may be attached to the body of a user, such as a patient or diabetic, at an attachment location and may deliver any therapeutic substance to a user at or around the attachment location. For example, a bottom surface of the wearable drug delivery device 708 may include an adhesive to facilitate attachment to the skin of a user as described in earlier examples.

The reservoir 738 may store liquid drugs, medications or therapeutic agents suitable for automated delivery, such as diabetes treatment drugs (e.g., insulin, glucagon, glucagon-like peptides), pain relief drugs (e.g., morphine), hormones, blood pressure medicines, chemotherapy drugs, or the like, such 786. The wearable drug delivery device 708 may include a needle or cannula (not shown) coupled to the reservoir 738 and extending into the body of the user for delivering a liquid drug into the user's body of the user (which may be done subcutaneously, intraperitoneally, or intravenously), and a pump mechanism 744 under control of the processor 748 that is operable to transfer the liquid drug from the reservoir 738 through the needle or cannula and into the user.

The power source 740, such as a battery, a piezoelectric device, other forms of energy harvesting devices, or the like, for supplying electrical power to the pump mechanism 744 and/or other components (such as the processor 748, memory 746, and the communication device 742) of the wearable drug delivery device 708.

In some examples, the wearable drug delivery device 708 may include a user interface 750, which may be a keypad, a touchscreen display, levers, light-emitting diodes, buttons on a top portion or side portion of the drug delivery device 708, a microphone, a camera, a speaker, a display, or the like, that is configured to allow a user to enter information and allow the drug delivery device 708 to output information for presentation to the user (e.g., alarm signals or the like). The user interface 750 may provide inputs, such as a voice input, a gesture (e.g., hand or facial) input to an optical sensor, swipes to a touchscreen, or the like, to processor 748 which the programming code interprets.

The wearable drug delivery device 708 may also include a device sensor 754 that may include an accelerometer, a gyroscope, a skin conductance measuring device, or the like. The device sensor 754 may be coupled to and provide inputs to the processor 748.

The smart accessory device 702 may be a smart watch, another wearable smart device, including eyeglasses or the like, a global positioning system-enabled wearable device, a wearable fitness device, smart clothing, or the like, and may be operable to communicate with the other components of system 700 via wireless communication links 770, 772, or 774.

For example, the smart accessory device 702 may include a communication device 736, a processor 734, a user interface 732 and a memory 730. The user interface 732 may be a graphical user interface presented on a touchscreen display of the smart accessory device 702. The memory 730 may store programming code to operate different functions of the smart accessory device 702 as well as an instance of the MDA 728. The processor 734 that may execute programming code, such as MDA 728 for controlling the wearable drug delivery device 708 to implement the processes and techniques of FIGS. 1-4 described herein.

The analyte sensor 704 may include a logic circuitry 758, a memory 762, a sensing/measuring device 782, a user interface 756, a power source 752, and a communication device 764. The analyte sensor 704 may be configured to detect multiple different analytes, such as lactate, ketones, uric acid, sodium, potassium, alcohol levels, blood glucose, proteins, hormones, or the like, and output results of the detections, such as measurement values or the like, for receipt by one or more of 702, 706 or 708.

The logic circuitry 758 of the analyte sensor 704 may be operable to perform many functions. For example, the programming code stored in the memory 762 may enable the logic circuitry 758 to manage the collection and analysis of data detected by the sensing and measuring device 782, such as blood glucose measurement values, providing trend information and the like. The memory 730 may be configured to store information and programming code, such as an instance of the AGC 760. The logic circuitry 758 may include discrete, specialized logic and/or components, an application-specific integrated circuit, a microcontroller or processor that executes software instructions, firmware, programming instructions, such as the AGC 760, stored in the memory 762), or any combination thereof. The logic circuitry 758 may be operable to implement and provide the functions described with reference to the examples of FIGS. 2, 4 and 5.

In an example, the analyte sensor 704 may be a blood glucose monitor removably attachable via adhesive, for example, to a body of the user. In such an example, the analyte sensor 704 is operable to measure a blood glucose measurement value of the user (not shown) and communicate with the controller 706 and the drug delivery device 708 via the communication device 764 under the control of the logic circuitry 758. The logic circuitry 758 may be operable to execute the AGC 760 that enables implementation of the processes 300, 400, 500 and 600 described above.

The analyte sensor 704 may, in an example, be operable provide blood glucose measurement values at selected set time intervals, such as 5 minutes, 4 minutes, 3 minutes, 2 minutes, 1.5 minutes, 1 minute, 30 seconds or near continuously, depending upon the selected setting. For example, at an initial setting of the AGC 760, the logic circuitry 758 of analyte sensor 704 may be operable to sample a user's blood glucose at a predetermined time interval, such as every 5 minutes, or the like, and output a blood glucose measurement value. The initial setting of the set time interval for the sensing/measuring device 782 to take samples and make measurements may be made via the user interface 756 or in response to control signals from the controller 706 or the wearable drug delivery device 708. In an example, the processor 714 of the controller 706 may cause a graphical user interface may be presented, via the user interface 716, that enables presentation of a recommendation for rescue carbohydrates to the user as described above.

The communication device 764 of analyte sensor 704 may have circuitry that operates as a transceiver for communicating the blood glucose measurement values to the controller 706 over the wireless link 784 or with the wearable drug delivery device 708 over the wireless communication link 768.

Services provided by cloud-based services 724 may include data storage that stores anonymized data, such as blood glucose measurement values, data related to insulin-to-carbohydrate ratios, correction factors, and other forms of data. The cloud-based services 724 may be accessed via the communication link 726 and the data network device 780, which may be a Wi-Fi device, a cellular communication tower, a local area network, a campus wide network or the like. The cloud-based services 724 may be responsive to inquires received from the MDA/AGC 710.

The wireless communication links 766, 768, 770, 772 and 784 may be any type of wireless link operating using known wireless communication standards or proprietary standards. As an example, the wireless communication links 766, 768, 770, 772 and 784 may provide communication links based on Bluetooth®, Zigbee®, Wi-Fi, a near-field communication standard, a cellular standard, or any other wireless protocol.

Software related implementations of the techniques described herein, such as the processes examples described with reference to FIG. 3, FIG. 4, FIG. 5 and FIG. 6 may include, but are not limited to, firmware, application specific software, or any other type of computer readable instructions that may be executed by one or more processors or logic circuitry. While the examples of FIG. 3, FIG. 4, FIG. 5 and FIG. 6 were primarily discussed as being implemented on a device, such as controller 706, the processes in the respective examples may be executable by the processor 748 of wearable drug delivery device 708 or the logic circuitry 758 of an analyte sensor 704. The programming code and/or computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed MDA/AGC application and algorithms may be operable to perform various functions related to open loop operations, such as the generation of prompts requesting the input of information such as weight or age. Similarly, inputs related to the foregoing processes and techniques may be received by the MDA/AGC application or algorithm from a user via a user interface. Other open-loop actions may also be implemented by adjusting user settings or the like in an MDA/AGC application or algorithm.

Some examples of the disclosed device or processes may be implemented, for example, using a storage medium, a computer-readable medium, or an article of manufacture which may store an instruction or a set of instructions that, if executed by a machine (i.e., processor, logic circuitry, or controller), may cause the machine to perform a method and/or operation in accordance with examples of the disclosure. Such a machine may include, for example, any suitable processing platform, computing platform, computing device, processing device, computing system, processing system, computer, processor, logic circuitry, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor, or logic circuitry, when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, logic circuitry, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A drug delivery system, comprising:

a processor; and a memory storing instructions that, when executed by the processor, enable the processor to:

determine that a blood glucose measurement value of a user is diverging from a target blood glucose range based on the blood glucose measurement value trending downwards from the target blood glucose range;

determine an after-insulin-on-board blood glucose measurement value for the user;

determine, by using the user's blood after-insulin-on-board glucose measurement value, an amount of rescue carbohydrates to be consumed by the user to maintain the user's blood glucose measurement value within the target blood glucose range; and output the determined amount of the rescue carbohydrates.

2. The drug delivery system of claim 1, wherein the stored instructions configure the processor to:

receive the user's blood glucose measurement value at a particular time;

obtain a target blood glucose measurement value setting for the user at the particular time;

determine a difference between the user's blood glucose measurement value at the particular time and the target blood glucose measurement value setting for the user at the particular time; and divide the difference by a correction factor of the user to obtain a modified difference value.

3. The drug delivery system of claim 2, wherein the stored instructions configure the processor to:

take a negative of the modified difference value;

determine an amount of insulin-on-board;

sum the negative of the modified difference value with the determined amount of insulin-on-board; and divide the sum by an insulin-to-carbohydrate ratio of the user to obtain the determined amount of the rescue carbohydrates.

4. The drug delivery system of claim 1, wherein the stored instructions configure the processor to:

obtain a default amount of carbohydrates from the memory; and set the default amount of carbohydrates as the amount of the rescue carbohydrates.

* * * * *